(12) United States Patent
Groner et al.

(10) Patent No.: US 6,221,671 B1
(45) Date of Patent: Apr. 24, 2001

(54) DIGITAL FLOW CYTOMETER AND METHOD

(75) Inventors: Warren Groner, Great Neck, NY (US); Jaspal Sanghera, Foxton (GB); Patrick Desfetes, Maisons-Alfort (FR)

(73) Assignee: Chemunex S.A., Maisons-Alfort (FR)

( * ) Notice: Subject to any disclaimer, the term of this patent is extended or adjusted under 35 U.S.C. 154(b) by 0 days.

(21) Appl. No.: 09/581,156

(22) PCT Filed: Dec. 11, 1998

(86) PCT No.: PCT/US98/25723
§ 371 Date: Aug. 14, 2000
§ 102(e) Date: Aug. 14, 2000

(87) PCT Pub. No.: WO99/31488
PCT Pub. Date: Jun. 24, 1999

Related U.S. Application Data

(60) Provisional application No. 60/069,528, filed on Dec. 12, 1997.

(51) Int. Cl.[7] .................................................. G01N 21/64
(52) U.S. Cl. .......................... 436/63; 422/82.08; 436/172; 356/73
(58) Field of Search ........................ 422/82.08; 436/63, 436/172; 356/72, 73

(56) References Cited

U.S. PATENT DOCUMENTS

| | | | | |
|---|---|---|---|---|
| 5,150,313 | * | 9/1992 | Van den Engh et al. | 364/569 |
| 5,483,469 | * | 1/1996 | Van den Engh et al. | 364/555 |
| 5,663,057 | * | 9/1997 | Drocourt et al. | 435/40.5 |
| 5,675,517 | * | 10/1997 | Stokdijk | 364/571.01 |
| 5,751,839 | | 5/1998 | Drocourt et al. | |

* cited by examiner

Primary Examiner—Jeffrey Snay
(74) Attorney, Agent, or Firm—Oblon, Spivak, McClelland, Maier & Neustadt, P.C.

(57) ABSTRACT

A system and method for testing for microbial contamination using a digital flow cytometer comprising an illumination source, a fluorescence detector, a digitizing device, and a digitized signal transferring device.

10 Claims, 9 Drawing Sheets

DIGITAL FLOW CYTOMETER AND METHOD

This application is a 371 of PCT/U.S. 98/25723 filed Dec. 11, 1998, and also claims benefit of Provisional No. 60/069,528 filed Dec. 12, 1997.

Technical Field

The present invention is addressed to an improved system for testing for microbial contamination in industrial products.

BACKGROUND ART

Adequate supervision of the safety of industrial products depends heavily on the detection of microbial contamination of the product. This microbial contamination can exist in a wide variety of industrial products including food, drinking water and health and beauty aids. A normal approach to detecting microbial contamination involves tests which depend upon the incubation of a sample taken from the product in a media which is suitable for the growth of micro-organisms. This approach involves the growth of microbes to ensure their viability and at the same time the multiplication of signals in order to simplify their detection. However, in many instances it requires several days to perform the test which imposes severe delays in manufacturing and inventory cost This is extremely critical in cases where the product is labile and the result of microbial testing is a shorter shelf life. Evidently then it is extremely important to develop ways of performing the microbial testing in a rapid manner.

Rapid testing methods which detect microbes without requiring a multiplication by growth usually involve labels which have been developed to effectively mark any viable micro-organism through the use of luminescence or fluorescence.

The general drawback with these methods has been the limit placed on the entire operation by the effectiveness of the instrumentation which must be capable of picking out the labeled microbe from other interfering signals with sufficient reliability to be useful in everyday practice. Practical use of such systems requires the ability to have a sensitivity to contamination which is very high detecting 100 or less microbes per milliliter of product. There is also a simultaneous requirement to have an extremely low false alarm rate of less than 1% for example.

One currently used instrumentation which has been attempted as a solution is a fluorescent flow cytometer wherein a diluted sample passes through a laser beam and photodetectors are used to note any fluorescence. Such a device when coupled with a prior device for fluorescently labeling each individual viable microbe, appears to be a useful tool in this area of microbial contamination detection. However, in spite of many attempts, this technology has not proved practical for a wide class of industrial products primarily due to the limitations in the sensitivity and/or specificity which arises.

The above discussed instrumentation and fluorescent labeling generally falls into two categories or two approaches to labeling the contaminating microbes. They both depend upon the action of a ubiquitous enzyme within the microbe-organism to create an optical signal. In one instance the resultant is a luminescent reaction while in the other instance the microbe is rendered fluorescent. The applicable use for either of these labeling method is limited by either the sensitivity of the luminescence method, so that enough light is not generated by a single microbe to be detected, or the specificity with regard to the fluorescent methods wherein any light from the labeled microbe cannot be distinguished from background fluorescent sources.

The automation of fluorescent methods of rapid microbiology yields two currently used approaches. In the fluorescent flow cytometry approach, a diluted suspension of a product to be tested is interrogated by passing it through a laser spot and detecting the resultant fluorescence of labeled microbes. On the other hand in the method known as the solid phase cytometry for instance as described in U.S. Pat. No. 5,663,057, a sample of a liquid product is passed through a membrane filter with sufficiently small pore size to retain any microbes and the filter is subsequently scanned by laser beam to detect any labeled microbes.

These two methods use different sampling means and address different products. For example some samples may not be filterable and thus cannot be used with the solid phase cytometer. Furthermore the level of performance which measures the sensitivity to the contaminating element which is obtained from the fluorescent flow cytometry is different from the solid phase cytometry. In fact, the solid phase cytometry is consistently more effective at detecting contamination. This difference is not due to the relative sensitivity but instead is due to the relative specificity. That is, both detectors have sufficient sensitivity to respond to a single microbe but the solid phase cytometer uses a set of sophisticated discriminators which are applied to a digitized waveform representing the fluorescent signal and these discriminators are based on the relative amplitude and detailed phase shape of individual fluorescent signals obtained at two or more optical wavelengths. It is for this reason that the solid phase cytometer is more effective at detecting contamination than the currently used fluorescent flow cytometers.

This difference in discrimination ability occurs because, when contrasted with the solid phase cytometers, the commercial fluorescent flow cytometer employ analog circuits which produce the feature values of the pulse waveform resulting from the particle fluorescence. This use of analog pulse processing limits the features which can be measured to their pulse integral, pulse height and pulse width. Thus, a significant amount of relevant information concerning the shape of the waveform is lost.

However it must be pointed out that, although digital processing has been applied to flow cytometers, its use has generally been limited by data processing speed. That is, when the sampling rate is made sufficiently high to obtain the required resolution for analyzing a single pulse, the processing system cannot keep up with the random pulse arrival rate. That is, the lowest sampling rate still produces an output for which continuous sampling is not possible. In order to resolve this issue a compromise in digital resolution is usually used and thus a compromise in the potential performance.

Yet another approach to obtaining additional information regarding the variation in fluorescent signals over time has been to use an array of detectors (linear CCD) which extend along the particle trajectories. In this method, the signal from each detector is processed in an analog manner and the results are combined to obtain a signal waveform. While this signal has been shown useful to measure the fluorescent decay it is a complicated system which must be precisely set up and it is limited by the relative sensitivity of adjacent detectors.

DISCLOSURE OF THE INVENTION

Accordingly one object of this invention is to provide a novel sampling strategy with a flow cytometer instrument in order to mitigate problems with data processing by interrupting the sampling interval in a digital flow cytometer periodically to allow data processing to keep up with the digital sampling rate.

It is a further object of the present invention to decouple the peak sampling rate from the average data transfer capacity and to maintain steady state conditions for the entire measurement, in order to provide a sample which will be representative even with the interrupted sample interval and wherein the sample size is determined by the cumulative sample interval.

It is a further object of the present invention to provide a technique which is particularly useful for a rapid microbiology wherein it is crucial to separate fluorescent signals originated from labeled microbes from those produced either by induced auto-fluorescence, free fluorescent dye or non-specific labeling.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

BEST MODE FOR CARRYING OUT THE INVENTION

Figure 1:
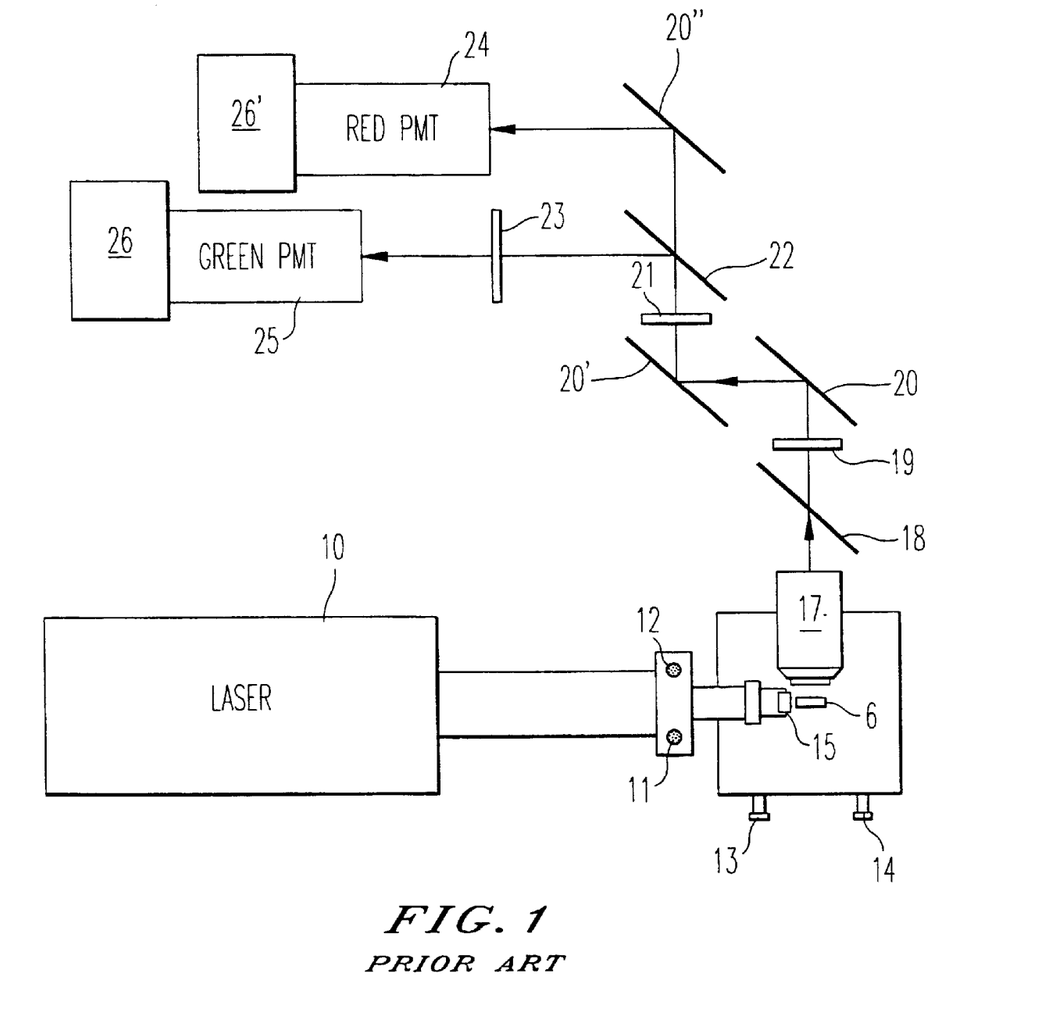
FIG. 1 illustrates a structural diagram of a conventional optical arrangement for use in the present invention.
Figure 2:
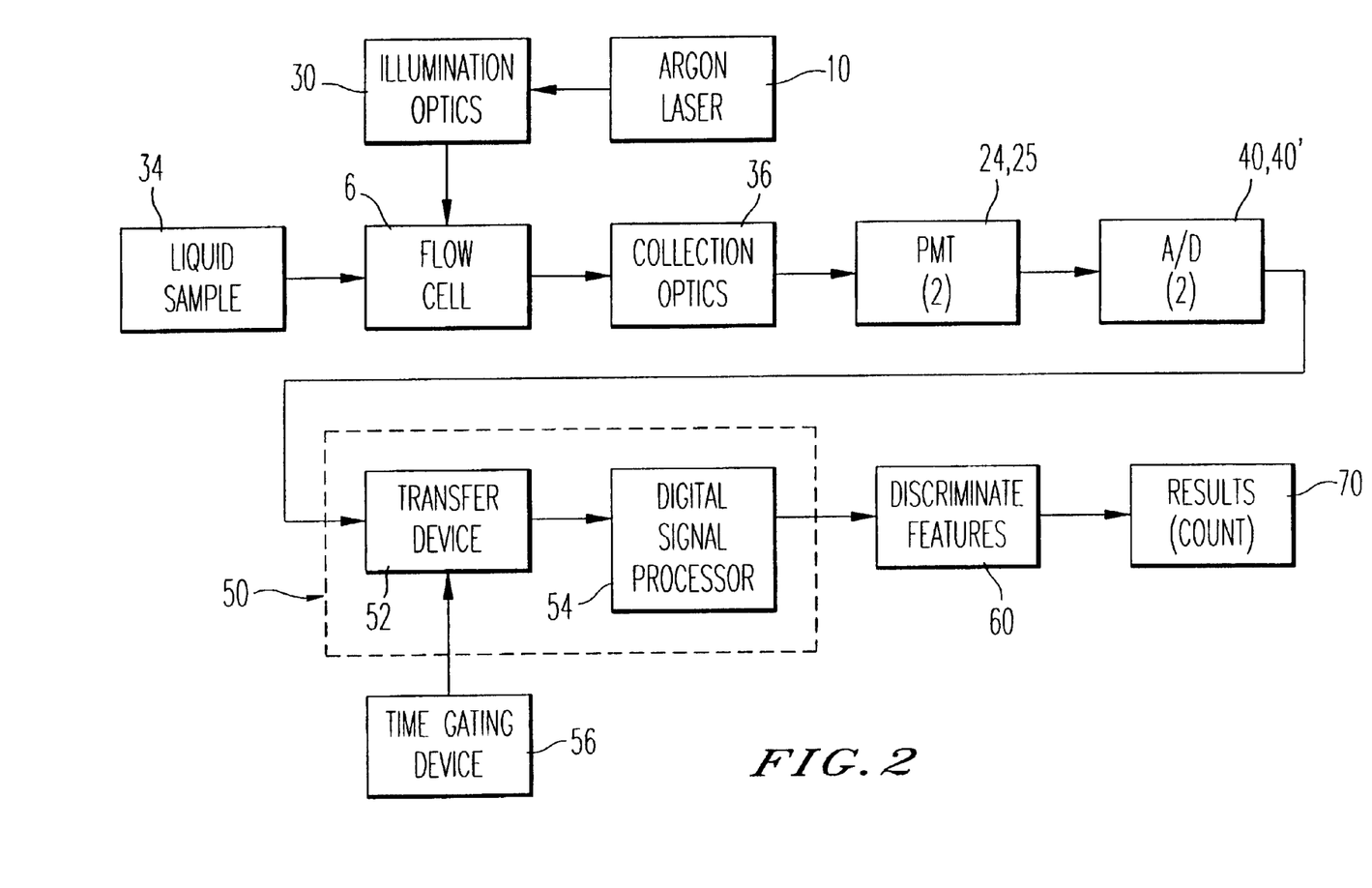
FIG. 2 is a functional block diagram of the digital flow cytometer of the present invention.

Referring now to the drawings, wherein like reference numerals designate identical or corresponding parts throughout the several views and more particularly to FIGS. 1 and 2 thereof, there is illustrated a layout of the optical structure 30 utilized for the digital flow cytometer and its operation in the present invention. The digital flow cytometer of the preferred embodiment is illustrated in the optical structure of FIG. 1 wherein light from an argon ion laser 10 is used to illuminate a flow stream of a vertical rectangular quartz flow cell 6. This flow stream contains diluted specimen 34 which have been previously labeled with a fluorescent dye sensitive to microbes and excited at 488 nm corresponding to the wavelength of the argon ion laser. The excitation can occur, for example, by using a substrate to the ubiquitous non-specific esterases which converts carboxyfluorescein to a fluorescent state. The position of the output beam from the laser 10 is controlled by the lateral position adjustment 11 and the vertical position adjustment 12. The positioning of the flow cell is controlled by the x position adjustment 13 and the y position adjustment 14. The output of the laser is focused by the optics 15 which is a cross cylinder lens providing an elliptical spot when focused at the center of the flow cell 6. The flow stream passes the illuminated spot at a velocity of approximately 8 meters per second with the illuminated spot having a bi-variate Gaussian intensitive profile with a smaller dimension of between 10 and 30 microns in the direction of flow and a longer dimension of between 60 and 100 microns orthogonal to the flow direction.

The fluorescence which results from the laser on the specimen is detected by an optical arrangement which includes an objective lens 17 positioned at a 90° angle to the illuminated beam. The detected fluorescent is split by a combination of mirrors onto two separate PMT (photo multiplier tube) detectors 24 and 25. The path between the objective lens 17 and the photo multiplier tubes 24 and 25 in an illustrative embodiment of FIG. 1 utilizes dichroic mirror 18, relay lens 19, non-selective mirrors 20 and 20' and a second imaging lens 21 which passes the image to a dichroic mirror 22 (having a long pass above 615 nm) and finally to another non-selective mirror 20". The red sensitive photo multiplier tube 24 receives the image from the mirror 20" and feeds it to a transimpedance preamplifier 26' while the photo multiplier tube 25 receives the image from the dichroic mirror 22 through the bandpass filter (510–540 nm). The outputs of each of the photo multiplier tubes 24 and 25 are fed to transimpedance preamplifiers 26, 26' in order to convert from current to voltage.

The signal train from the two photo multiplier tubes 24 and 25 and the preamplifiers 26 and 26' are then converted through respective a/d converters 40 and 40' as shown in FIG. 2. These a/d converters are 12-bit converters which function at a sampling rate of 5 MHZ. The output of the A/D converters are fed to a transfer device 52 which functions to provide interruption by way of the time gating device 56 according to a particular interruption scheme.

Figure 4:
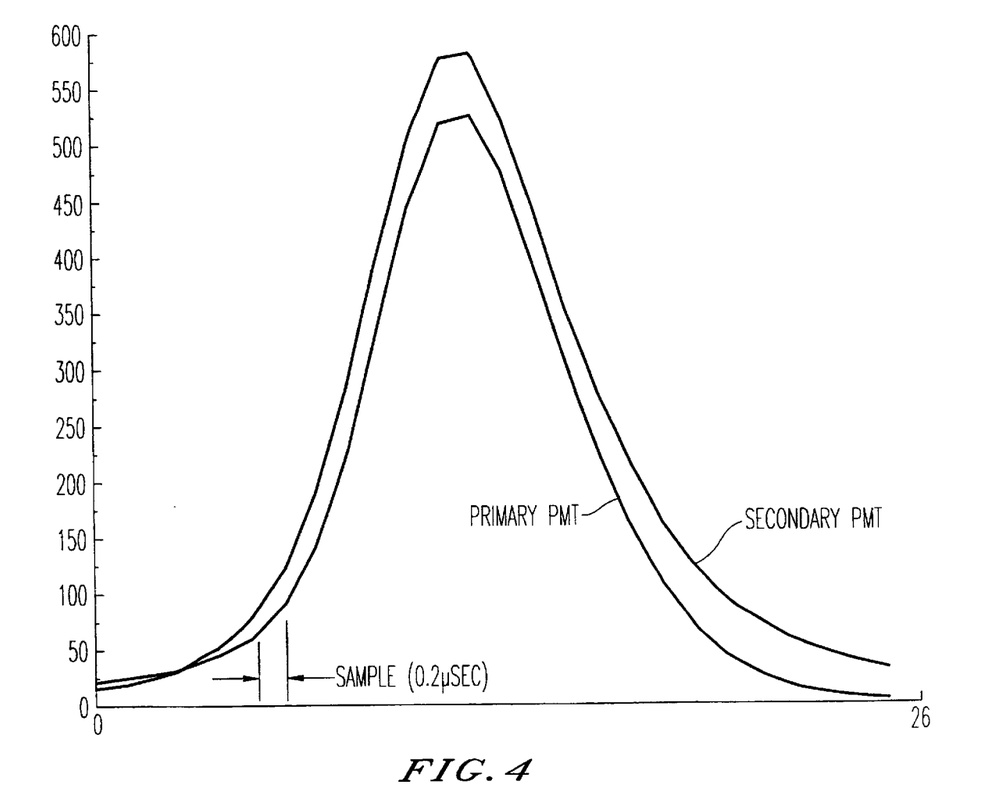
FIG. 4 illustrates a fluorescent pulse intensity profile over time.

The characteristics of a typical fluorescent signal amplitude curve, as shown in FIG. 4, are obtained from a fluorescent labeled microbe under the conditions described with respect to FIG. 1.

Figure 5:
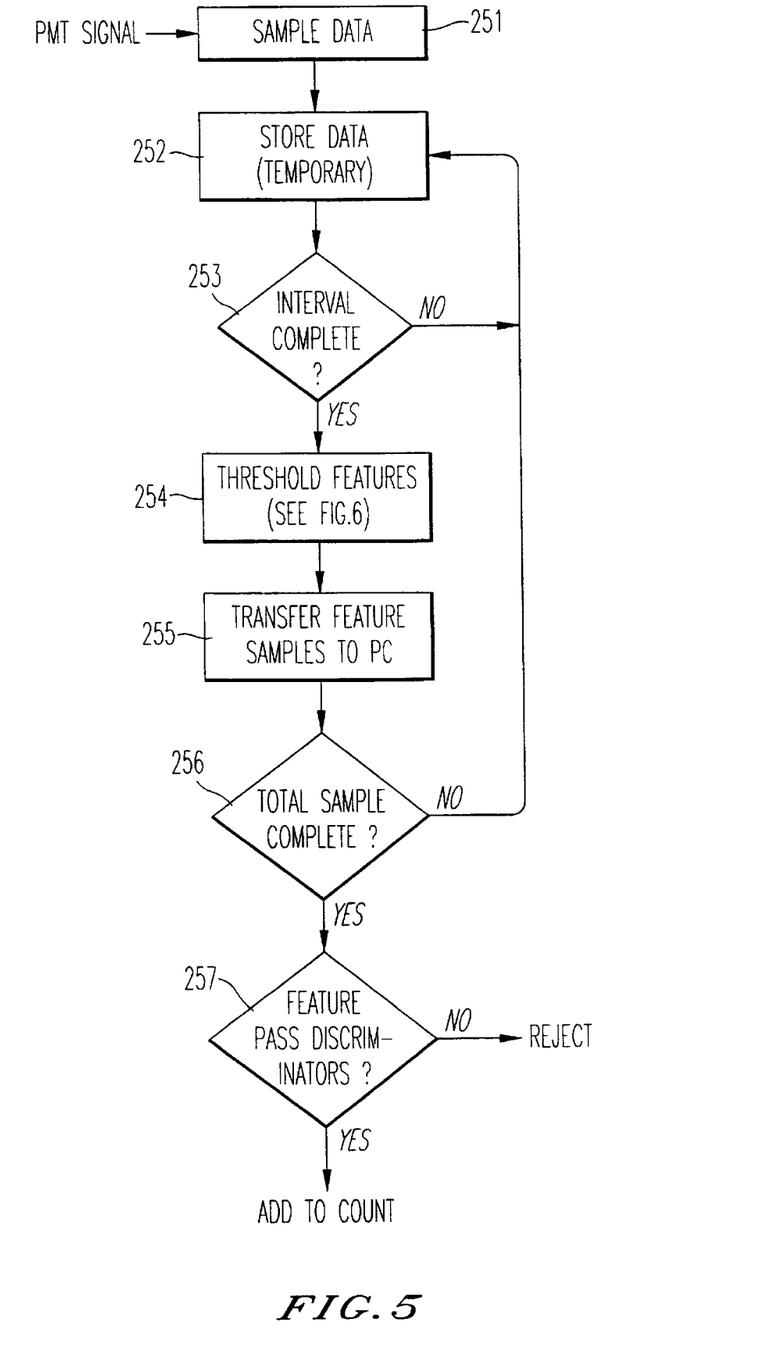
FIG. 5 is a flowchart illustrating the operation of the digital discrimination according to the present invention.
Figure 6:
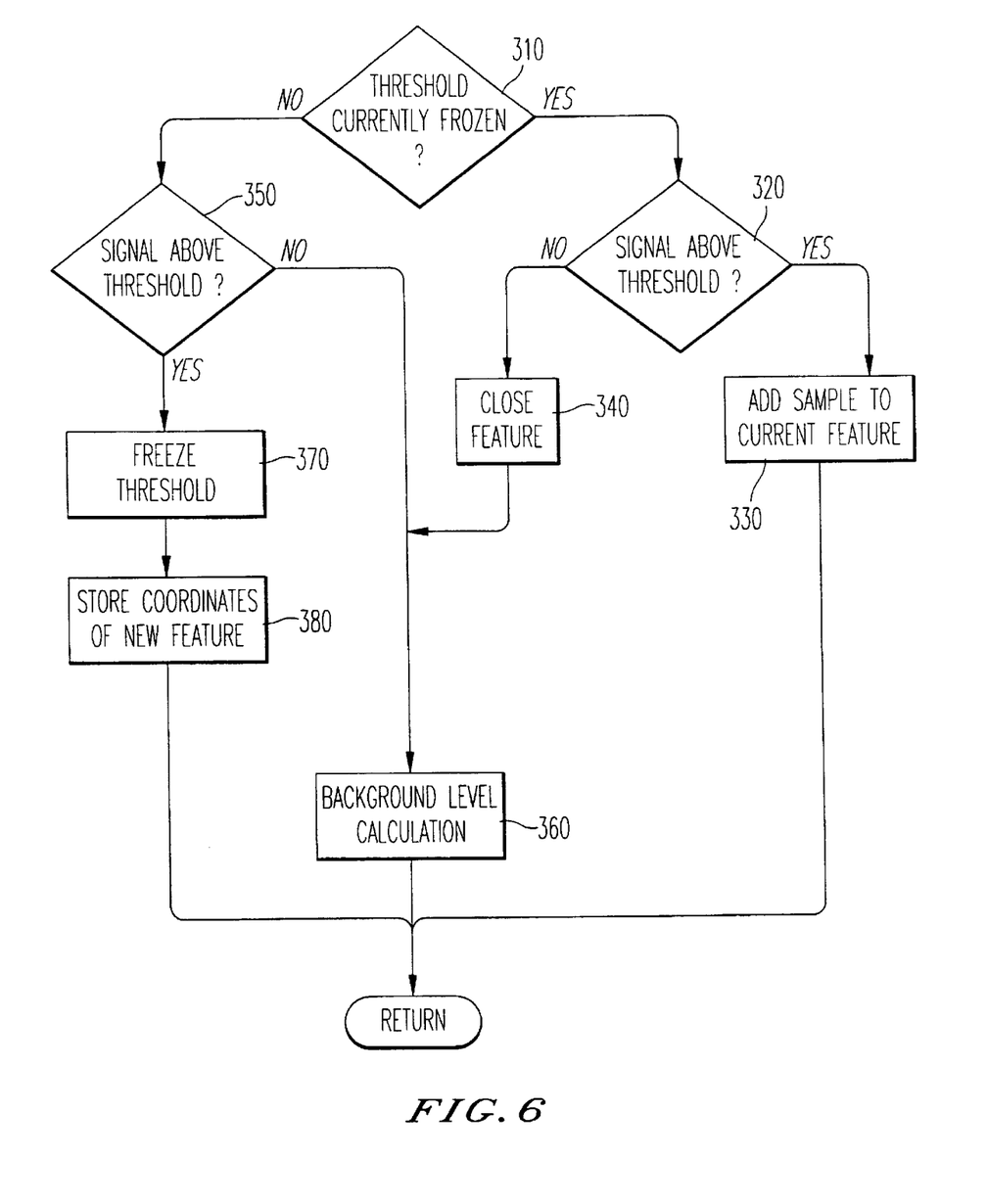
FIG. 6 is a flowchart illustrating the feature detection method according to the present invention.

Transfer and processing of the digital signals according to the present invention is illustrated in FIG. 5. Complete sampling data 251 from each of the two photo multiplier tubes 24 and 25, during a total sampling time of approximately 18 milliseconds (T of FIG. 3), is gated by time gate 56 in FIG. 2, into a temporary storage buffer 252. Subsequently, when a shorter sampling interval (t of FIG. 3) is complete, the threshold features are determined at 254 as will be described with respect to FIG. 6. Then the feature samples are transferred for computation at 255 and the total sample is tested for completion to see whether the total sampling time T (FIG. 3) has been complete as indicated at 256. If the total sampling time has not been completed, then another interval of two milliseconds is tested until the total sample time has been completed at which time the feature pass discriminators 257 determine whether the feature is to be added to the count or rejected. Furthermore, after each sampling interval, the data flow is interrupted (g of FIG. 3). During the shorter sampling interval (t) a moving threshold algorithm, as detailed in the flowchart of FIG. 6, is used to isolate regions (features) in which the fluorescent signal exceeds expectations and the sample points from each feature are then transferred into a computer for further discrimination. As shown in FIG. 6 a threshold is determined at 310. If a signal is above a currently frozen threshold as indicated at step 320, then the sample is added to the current feature as indicated at 330. On the other hand, if the signal is not above the currently frozen threshold, the feature is closed as indicated at 340 and added to the background level calculation 360. If the current threshold is not frozen at 350, then if the signal is above the threshold then the threshold is indeed frozen at 370 with a subsequent storing of a new feature at 380. If the signal is not above the unfrozen threshold as determined at 350, then the signal is added to the background level calculation 360. When this process is complete a new measurement interval (t) is begun. This alternation of sampling interval (t) and interrupted time (g) continues until the end of the total sampling time (T). This interval is typically 3,000 cycles. The stored features are then analyzed by a set of discriminating algorithms 60.

This system resulted from a comparison of the differences between solid phase cytometry and flow cytometry which initially indicated that the peak data transfer rate was essentially the same between the two systems. This unexpected result led to a realization that the difference between the two systems was in the average data transfer rate. In the solid phase system, the scanning is performed through the use of driven mirrors so that the initiation of each scan line was controlled by a signal. Typically, the scan retrace time was used to buffer the data transmission rate. A new scan in the solid phase system was only started when the processor had caught up with data from the previous scan. Because the entire membrane was scanned no data was lost but the scanning period was variable.

In contrast, in the flow cytometer system, the diluted specimen was analyzed for a predetermined interval of time. This interval is initiated after steady flow condition is established with the diluted specimen passing the detection station. It is assumed that, provided the steady state conditions are maintained during the sampling interval, a representative sample has been obtained. The size of the analyzed sample is proportional to the length of the sampling interval.

Figure 3:
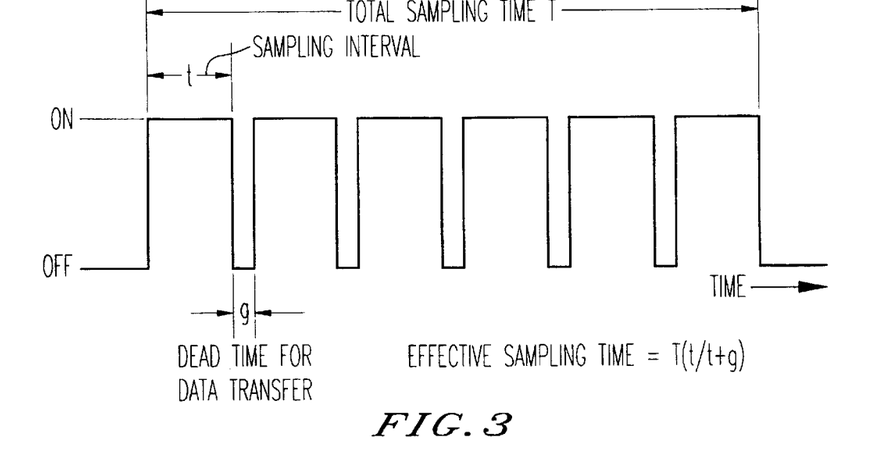
FIG. 3 is an illustration of the sampling scheme used in the digital flow cytometer of the present invention.

The present invention is based upon the employment of the unique sampling strategy discussed with respect to the FIG. 3 for use with a flow cytometer instrument in order to mitigate the problem with respect to data transfer. More specifically, the interruption (g) in the sampling interval in a digital flow cytometer occurs periodically in order to allow the data transfer and processing to keep up with the digital sampling rate. The effect is to decouple the peak sampling rate from the average data transfer capacity. As long as the steady state conditions are maintained for the entire measurement period, the sample will still be representative and the sample size will be determined by the cumulative sample interval. This system can be used with any degree of digital resolution. In order to use higher resolutions, either the rate or duration of the interruptions need to be increased so that the same average data transfer rate can be maintained. Thus, with higher resolution, the cumulative sample interval must be extended. This technique is especially useful when the digital flow cytometer is used for Rapid Microbiology. In this case, it is crucial to separate fluorescent signals originating from labeled microbes from those produced either by induced auto-fluorescence or from free fluorescent label.

One of the keys to this discrimination is the size of the particle which is represented in the shape of the fluorescent pulse (intensity vs time). Microbes are very small compared to the laser spot. Thus, when they pass the illuminated region, the shape of the resultant fluorescent pulse accurately reflects the Gaussian distribution of intensity as shown in the example of FIG. 4. This is important because the Gaussian distribution of intensity is a characteristic of the laser beam. On the other hand, larger objects generally display extended non-Gaussian intensity profiles. Free fluorescent label causes variations in fluorescent intensity which are essentially random and thus are also non-Gaussian. Therefore, a discriminator which analyzes the fluorescent intensity waveforms and compares them to a Gaussian distribution is an effective means of discrimination of the fluorescence from the microbial particles.

Effective discrimination is also affected by the fluorescent lifetime. Fluorescent labels can be chosen with fluorescent lifetimes which are substantially longer than characteristic auto-fluorescence. In this case, by comparing the fluorescent pulse to the illuminating intensity (as measured by the scattering of illuminating light) in time, the differences may be related to the fluorescent lifetime. Short fluorescent lifetimes of less than 10 nanoseconds may be distinguished from the longer lifetimes. Finally, effective discrimination is related to the time correlation between fluorescent intensity at two wavelengths. In the case of a discrete particle such as a labeled microbe, the peak intensity in two channels is highly correlated while, on the other hand, the random fluctuations resulting from free fluorescent labeling in the specimen is not well correlated between the two fluorescent channels.

Figure 7:
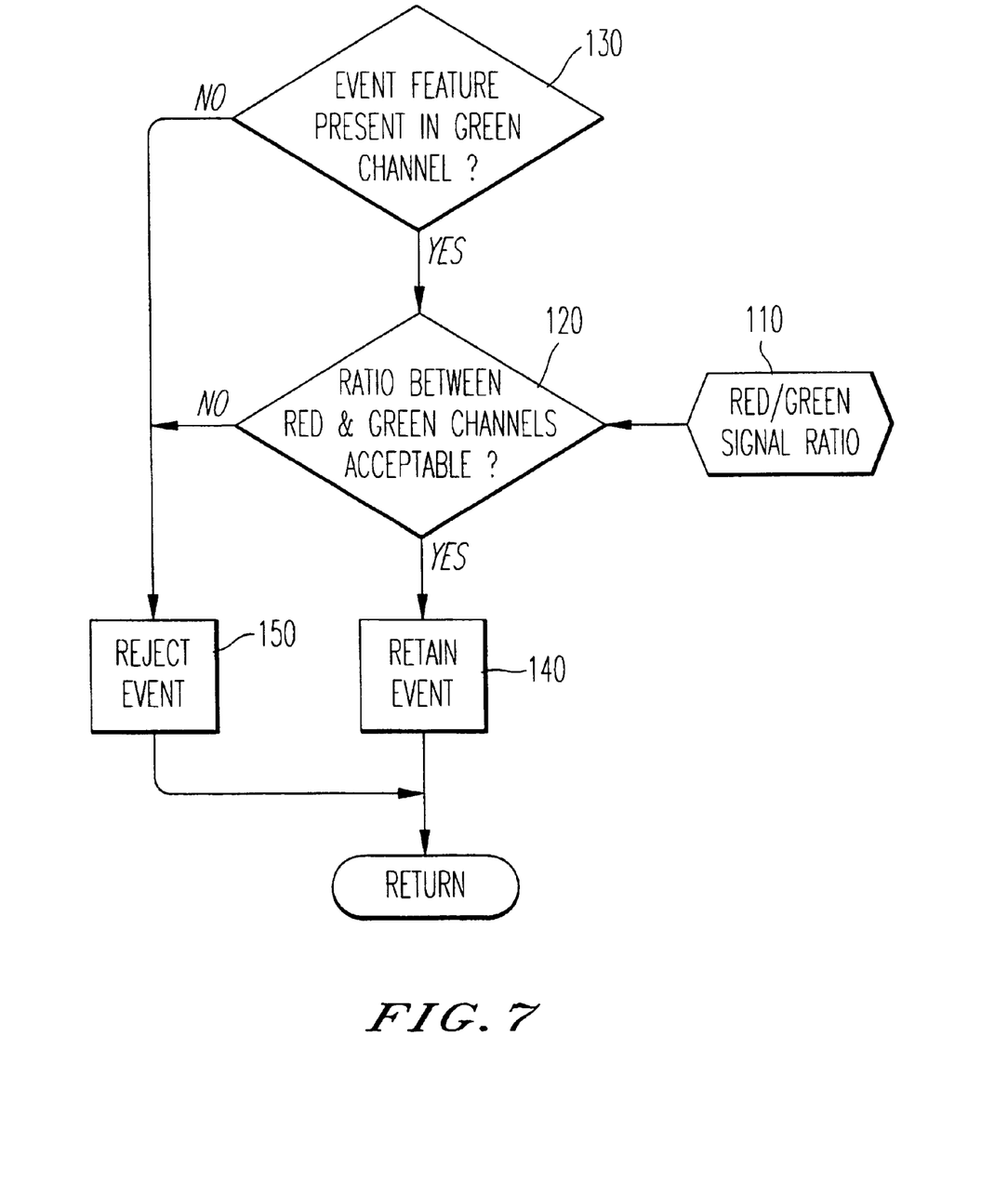
FIG. 7 is a flowchart of the color ratio discrimination method according to the present invention.
Figure 8:
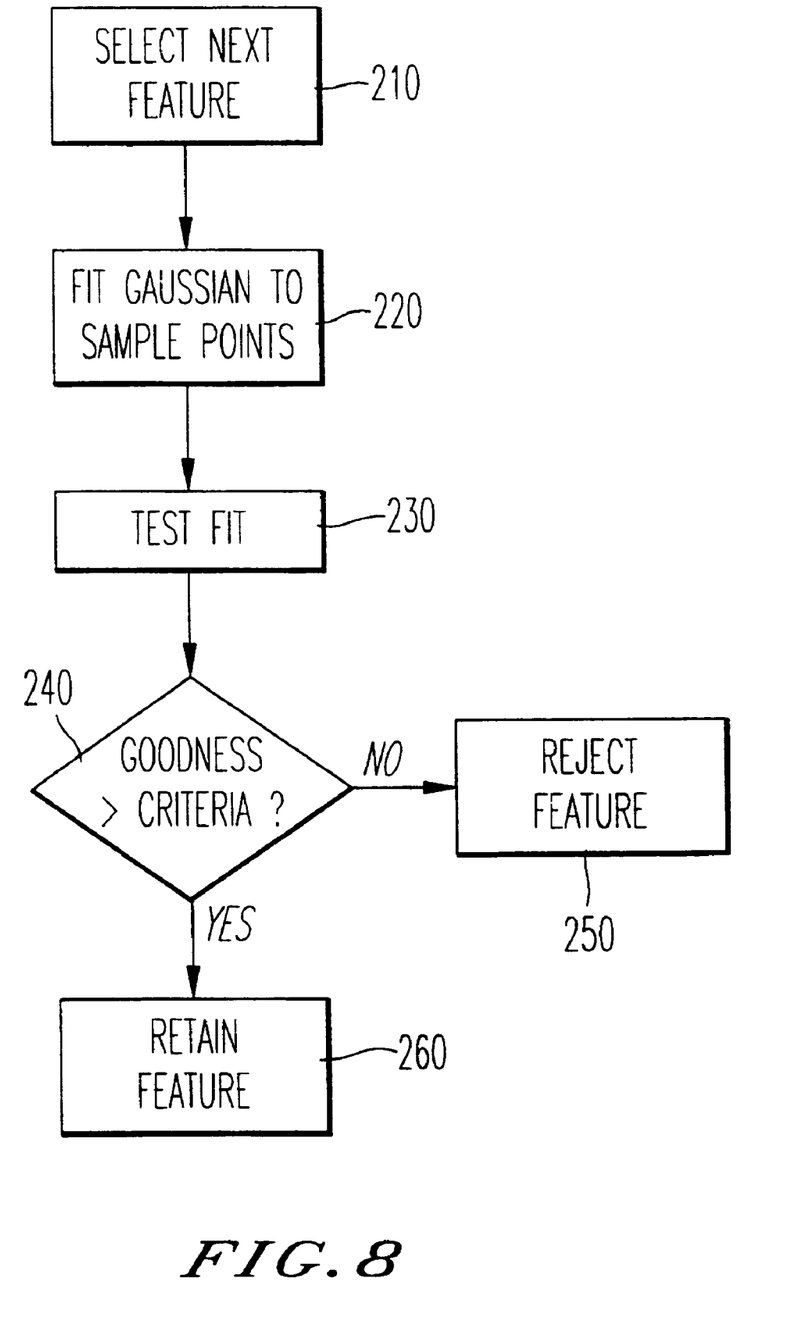
FIG. 8 is a flowchart illustrating the Gaussian discriminator method employed in the present invention.

Therefore, the stored features in the discriminating feature section 60 of FIG. 2 are analyzed by a set of discriminating algorithms including a color ratio discrimination detailed in FIG. 7 and a Gaussian profile discrimination detailed in FIG. 8. With respect to the color ratio discrimination of FIG. 7, the ratio of each sample point in the green signal is compared to the signal level in the red channel and a ratio is formed. This ratio is compared to the ratio expected from the spectrum of the fluorescent dye used in labeling bacteria. If the ratio exceeds the expected limit, the feature is rejected as being consistent with auto-fluorescence as opposed to specific labeling. More particularly, the red/green signal ratio at 110 is compared with an acceptable ratio at 120 if there is also an event feature present in green channel 130. If the ratio is within acceptable boundaries and if the feature event is present in the green channel, then the event is retained at 140. On the other hand, if there is no event feature present in the green channel or the ratio between the red and green channel signal is outside of acceptable ranges, the event is rejected at 150.

With respect to the other discrimination algorithm shown in FIG. 8, the Gaussian profile discriminator fits sample points in each feature to a Gaussian curve. Because the laser beam intensity is a Gaussian profile, fluorescent signal from objects which are very small compared to the dimensions of the laser spot will reproduce a Gaussian intensity profile while larger objects will be typically non-Gaussian in their intensity profile. Because all labeled microbes can be expected to be very small compared to the laser spot, those features having non-Gaussian profiles (indicated by the measure of "goodness") are rejected. More particularly, as shown in FIG. 8 after a feature is selected at 210, it is fit into a Gaussian in order to sample points at 220 and then the test fit is determined at 230 while its "goodness" criteria is subsequently checked as to whether it is a non-Gaussian profile at 240. If it is a non-Gaussian profile, it is rejected at 250 while on the other hand, if it is a Gaussian profile fit, then the feature is retained as being a labeled microbe at 260.

In addition to the above discussed key discriminators of FIGS. 7 and 8, a number of other discriminating criteria may be applied to the stored data in order to enhance discrimination between fluorescent labeled microorganisms and other spurious interfering signals. These may be applied either one at a time or in combination. For example, the feature length which indicates a number of digital samples in the pulse at the half power point may be used as a discriminator as well as the specific intensity which is a measure of the peak intensity divided by the feature length. Furthermore, the symmetry, which is the rate of rise of fluorescence compared to fluorescent decay, and the correlation corresponding to the peak intensity in one or more fluorescent channels may also be utilized as a way of further enhancing the discrimination. After features associated with each specimen have passed through the discriminating criteria they are then enumerated and the results displayed as a count at 70 shown in FIG. 2.

In order to analyze the improvement brought about by the digital flow cytometer of the present invention it is helpful to begin by recognizing some of the key times involved in the process of analyzing approximately 100 microliter of a specimen as detailed in Table 1.

TABLE 1

| EVENT OR PROCESS | TYPICAL TIME |
|---|---|
| PARTICLE TO PASS LASER SPOT | 1.2 usec |
| EACH DIGITAL SAMPLE | 0.2 usec |
| SAMPLING INTERVAL (typical) | 18,000 usec |
| INTERRUPT INTERVAL (approx) | 10,000 usec |
| TOTAL MEASUREMENT PERIOD | 43 seconds |

Figure 9:
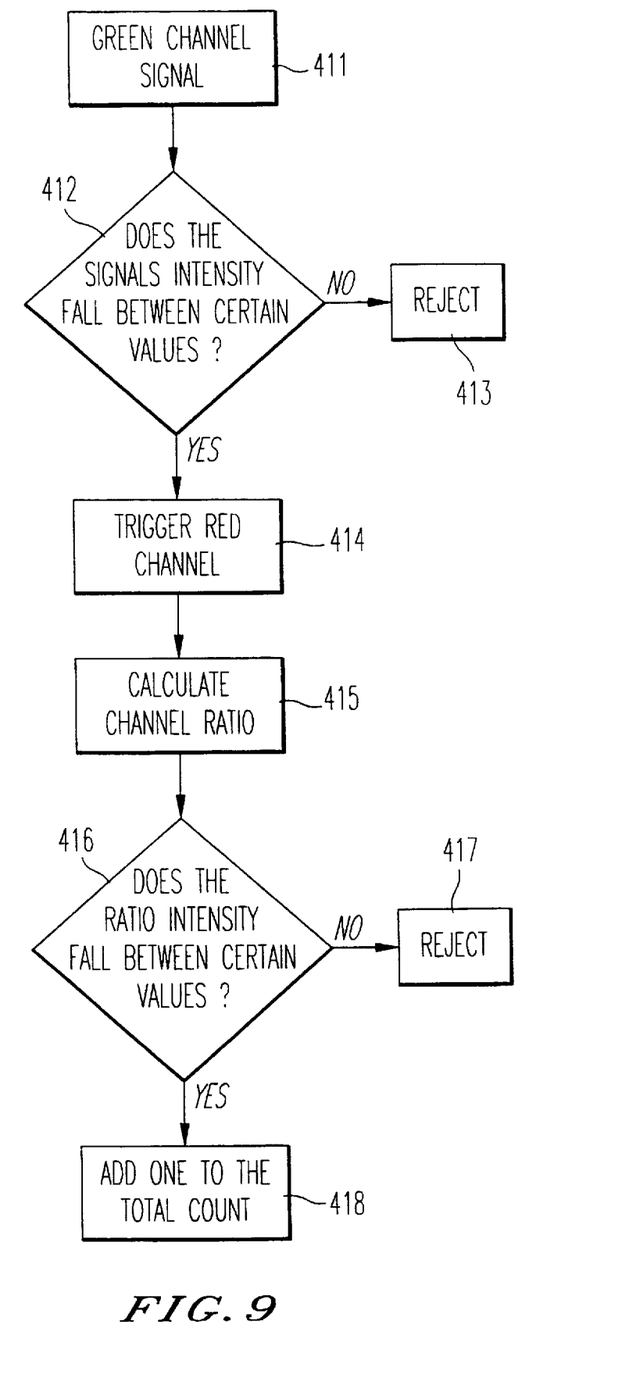
FIG. 9 is a flowchart illustrating operation of an analog discriminator.

Based on the events and the typical occurrences of Table 1, an experiment was conducted to demonstrate the digital processing scheme of the present invention in comparison with an analog processing of the same samples. For the purpose of this experiment, analog signals were split at the output of each photo multiplier tube with one set analyzed by the digital scheme described above and the other analyzed by a typical analog processing algorithm. A typical analog processing algorithm and its logic is shown in FIG. 9 wherein a green channel signal at 411 is tested at 412 to determine whether the signal intensity falls between predetermined values. If it does not then the signal is rejected at 413. If the green channel signal does fall between the predetermined values, the red channel is triggered at 414 and the channel ratio is calculated at 415. If this calculated ratio intensity falls between other predetermined values as indicated at 416, then one is added to the total count at 418. If does not fall within these predetermined values, then the signals are rejected at 417.

A comparison of the discrimination results from the digital flow cytometer time scheme and subsequent discrimination determination of the FIGS. 7 and 8, of the present invention when compared with the analog feature detection of FIG. 9 is displayed in the Table 2.

TABLE 2

| DISCRIMINATOR | ANALOG | DIGITAL |
|---|---|---|
| GREEN PEAK INTENSITY | X | X |
| GREEN/RED PEAK INTENSITY RATIO | X | X |
| GREEN/RED INTEGRAL RATIO | — | X |
| GAUSSIAN FIT | — | X |
| FEATURE LENGTH | — | X |

This Table 2 reveals the discrimination capabilities of the digital system when compared with the analog system. The results were compared for a number of test specimens as well as some specimens typically encountered in testing industrial products for microbial contamination. Results were also compared for detection of specifically labeled fluorescent beads of approximately 0.2 micron diameter which were used to stimulate bacteria. The results obtained are tabulated in Table 3 where it can be seen that although the results are equivalent when the specimen consist of simply clean water or water spiked with fluorescent particles, the digital processing scheme is much more effective in eliminating spurious counts from auto-fluorescence present in unlabeled specimens without compromising detecting of bacteria.

TABLE 3

| SPECIMEN | EXPECTED COUNT | ANALOG COUNT (AVERAGE) | DIGITAL COUNT (AVERAGE) |
|---|---|---|---|
| WATER BLANK (2 specimens) | 0 | 2 | 2 |
| FLUORESCENT BEADS IN WATER (3 specimens) | 400 | 433 | 414 |
| E-COLI IN WATER | >100 | 9230 | 109 |
| E-COLI IN WATER | >100 | 364 | 318 |
| E-COLI IN WATER | >100 | 3218 | 261 |
| CHOCOLATE DRINK UNLABELED (9 specimens) | 0 | 958 | 3 |
| FLUORESCENT BEADS IN CHOCOLATE DRINK (6 specimens) | 300 | 388 | 278 |
| COSMETIC UNLABELED (5 specimens) | 0 | 1154 | 0 |
| FLUORESCENT BEADS IN COSMETIC (approx 500/specimen) | 500 | 952 | 519 |
| E-COLI IN COSMETIC | >100 | 95 | 109 |

Another experiment determined discrimination from free fluorescent labeling. In this experiment the analysis of free fluorescein in solution was compared to the signals obtained from fluorescein labeled beads. The intensity of free fluorescein was adjusted so that the same average fluorescent signal was obtained. Because the color of the free fluorescein and the beads was the same, approximately the same ratio of intensity was obtained between the two fluorescent channels. Table 4 illustrates the comparison between the two specimens when the additional digital discriminators are considered:

TABLE 4

| DISCRIMINANT | FREE FLUORESCEIN | FITC LABELED BEADS |
|---|---|---|
| AVERAGE PEAK (ADC COUNTS) | 314 | 186 |
| COLOR RATIO | 0.8 | 0.8 |
| PULSE HALF WIDTH (SAMPLES) | 24 | 12 |
| CORRELATION (PMT1 vs PMT2) | 0.289 | 0.90 |
| GAUSSIAN FIT (ERROR) | 776 | 537 |
| SPECIFIC INTENSITY | 12.7 | 23.9 |

When discrimination parameters were set on the basis of the last four discriminators alone, an acceptance of greater than 60% was obtained for the FITC labeled beads while only 0.04% of the signals from the free fluorescein were accepted. Thus, a discrimination ratio of greater than 1500 between beads and free fluorescein was obtained for signals having similar integrated pulse amplitude and similar color ratio. Thus, these results illustrate the clear improvement resulting from the additional digital discriminators.

The present invention includes a computer program product which is a storage medium including instructions which can be used to program a computer to perform processes of the invention. The storage medium can include, but is not limited to, any type of disk including floppy disks, optical discs, CD-ROMs, and magneto-optical disks, ROMs, RAMs, EPROMs, EEPROMs, magnetic or optical cards, or any type of media suitable for storing electronic instructions.

Figure 10:
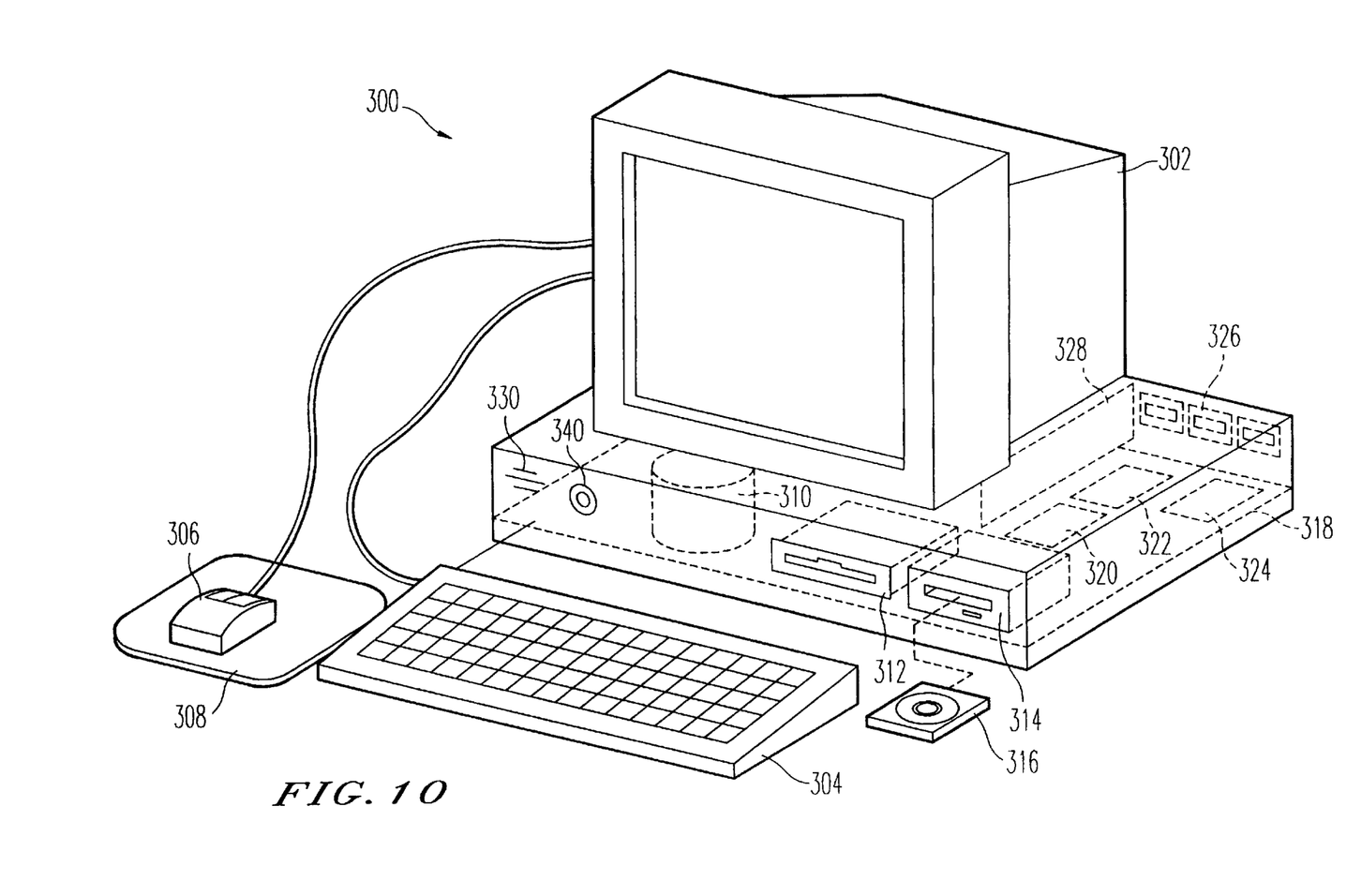
FIG. 10 is a schematic illustration of a general purpose computer 300 programmed according to the teachings of the present invention.

FIG. 10 is detailed schematic diagram of a general purpose computer 300 which could be used to accomplish the functions of the transfer device 52, the digital signal processor 54, the time gating 56 and the discriminator 60 of FIG. 2. In FIG. 10, the computer 300, for example, includes a display device 302, such as a touch screen monitor with a touch-screen interface, a keyboard 304, a pointing device 306, a mouse pad or digitizing pad 308, a hard disk 310, or other fixed, high density media drives, connected using an appropriate device bus, such as a SCSI bus, an Enhanced IDE bus, a PCI bus, etc., a floppy drive 312, a tape or CD ROM drive 314 with tape or CD media 316, or other removable media devices, such as magneto-optical media, etc., and a mother board 318. The motherboard 318 includes, for example, a processor 320, a RAM 322, and a ROM 324, I/O ports 326 which are used to couple to the image acquisition device 200 of FIG. 1, and optional specialized hardware 328 for performing specialized hardware/software functions, such as sound processing, image processing, signal processing, neural network processing, etc., a microphone 330, and a speaker or speakers 340.

Stored on any one of the above described storage media (computer readable media), the present invention includes programming for controlling both the hardware of the computer 300 and for enabling the computer 300 to interact with a human user. Such programming may include, but is not limited to, software for implementation of device drivers, operating systems, and user applications. Such computer readable media further includes programming or software instructions to direct the general purpose computer 300 to perform tasks in accordance with the present invention.

The programming of general purpose computer 300 may include a software module for digitizing, transferring, interrupting, signal processing and discriminating as detailed in FIG. 2. Alternatively, it should be understood that the present invention can also be implemented to process digital data transferred by other means.

The invention may also be implemented by the preparation of application specific integrated circuits or by interconnecting an appropriate network of conventional component circuits, as will be readily apparent to those skilled in the art.

Obviously, numerous modifications and variations of the present invention are possible in light of the above teachings. It is therefore to be understood that within the scope of the appended claims, the invention may be practiced otherwise than as specifically described herein.

What is claimed is:

1. An apparatus for detecting and counting fluorescent particles, comprising:

an illuminating source providing a fluorescence stimulating beam;

means for supplying a suspension containing fluorescently labeled particles to pass through said beam at a high velocity;

means for detecting fluorescence of said particles and converting said fluorescence into electrical signals;

means for digitizing said electrical signals wherein said digitizing occurs at a rate sufficient to reproduce an intensity profile of an individual fluorescent particle passing said stimulating beam;

means for transferring said digitized signals and means for providing interruptions of said transferred digitized signals and outputting digitized data to a digital signal processor, wherein a duration of each of said interruptions is a function of the operating speed of said digital signal processor in order to facilitate the transfer of digital information whereby the interruptions cause transfer and processing of data to be matched with the digital sampling rate of the digitizing means;

means for analyzing digitized data output from said signal processor whereby particles are distinguished from background noise.

2. The apparatus according to claim 1, wherein said means for detecting fluorescence and converting said fluorescence includes at least two photomultiplier tubes.

3. The apparatus according to claim 1, wherein said means for transferring includes a storage buffer for continuous storage at high rates for a predetermined measurement interval.

4. The apparatus according to claim 1, wherein said means for analyzing includes a moving threshold discrimination means for discriminating fluorescence features which functions to provide a discriminative fluorescence feature when a fluorescence intensity level exceeds a local average value.

5. The apparatus according to claim 2, further including a means for providing a comparison ratio of outputs of said at least two photodetectors.

6. A method for detecting and counting fluorescent particles, comprising the steps of:

providing a suspension containing fluorescently labeled particles at a high velocity;

providing a fluorescence stimulating beam;

detecting resulting fluorescence of said particles and converting said fluorescence into electrical signals;

digitizing said electric signals at a digitizing rate sufficient to reproduce an intensity profile of an individual particle in said suspension as it passes said stimulating beam at high velocity and outputting digitized signals;

transferring said outputted digitized signals and intermittently interrupting said digitized signals to provide digital data;

performing a digital signal processing on said digital data wherein the interrupting of said digitized signals occurs for a period of time which is a function of a speed of operation of said digital signal processing in order to facilitate the transfer of digital information whereby the interruptions cause transfer and processing of data to be matched with the digital sampling rate of the digitizing of said electric signals;

analyzing data output from said digital signal processing whereby particles are distinguished from background noise.

7. Method according to claim 6 wherein said step of detecting fluorescence and converting said fluorescence into electrical signals include the use of at least two photomultiplier tubes to provide two different wave lengths.

8. The method according to claim 6 wherein said step of transferring includes the step of storing at high rates for a predetermined measurement interval.

9. The method according to claim 6 wherein said step of analyzing includes a step of discriminating fluorescent features by moving threshold which functions to provide a discriminating fluorescent feature whenever a fluorescent intensity level exceeds a local average value.

10. Method according to claim 7 further including the step of providing a comparison of outputs of said at least two photodetectors.

* * * * *